(12) United States Patent
Friedt et al.

(10) Patent No.: US 7,440,085 B2
(45) Date of Patent: Oct. 21, 2008

(54) APPARATUS AND METHODS FOR SIMULTANEOUS SURFACE ACOUSTIC WAVE AND SURFACE PLASMON RESONANCE MEASUREMENTS

(75) Inventors: Jean-Michel Friedt, Neuilly sur Seine (FR); Andrew Campitelli, Melbourne (AU); Laurent Francis, Grez-Doiceau (BE)

(73) Assignee: Interuniversitair Microelektronica Centrum (IMEC), Leuven (BE)

( * ) Notice: Subject to any disclaimer, the term of this patent is extended or adjusted under 35 U.S.C. 154(b) by 373 days.

(21) Appl. No.: 11/313,606

(22) Filed: Dec. 20, 2005

(65) Prior Publication Data
US 2006/0173636 A1    Aug. 3, 2006

Related U.S. Application Data

(63) Continuation of application No. PCT/BE2004/000090, filed on Jun. 21, 2004.

(30) Foreign Application Priority Data
Jun. 20, 2003    (EP) ............................... 03447165.6

(51) Int. Cl.
*G01N 21/00*    (2006.01)
*G01N 21/55*    (2006.01)

(52) U.S. Cl. ........................................ 356/72; 356/445
(58) Field of Classification Search .................... 356/72
See application file for complete search history.

(56) References Cited

U.S. PATENT DOCUMENTS 5,588,428 A    12/1996 Smith et al.
6,161,437 A *  12/2000 Brennan et al. ............... 73/655
2002/0173922 A1  11/2002 Potyrailo

FOREIGN PATENT DOCUMENTS

JP    55037910    3/1980

(Continued)

OTHER PUBLICATIONS

Laschitsch Alexander, et al., "Simultaneous Determination of Optical and Acoustic Thicknesses of Protein Layers Using Surface Plasmon Resonance Spectroscopy and Quartz Crystal Microweighing," Oct. 2, 2000, Applied Physics Letters, America Institute of Physics, pp. 2252-2254.

(Continued)

*Primary Examiner*—F. L Evans
(74) *Attorney, Agent, or Firm*—Knobbe Martens Olson & Bear LLP (57) ABSTRACT

The invention relates to a method and apparatus for obtaining and analysing physical properties of a substance. Optical data and acoustical data are obtained for the substance and the data are used to apply a model of the optical/acoustical properties of the substance such that thereby any of the thickness, the density, the refractive index and composite related information such as the content of a certain component in the substance can be determined. If dynamic effects are studied, preferably data of simultaneously performed optical and acoustical measurements are used. An example is the use of data of surface plasmon resonance measurements and surface acoustic wave measurements to determine the water content in solutions of organic material.

28 Claims, 7 Drawing Sheets

FOREIGN PATENT DOCUMENTS

| | | |
|---|---|---|
| JP | 11148883 | 6/1999 |
| JP | 2002153472 | 5/2002 |

OTHER PUBLICATIONS

Malik et al., "Multisensor Integration for Underwater Scene Classification," Oct. 13, 1991, Decision Aiding for Complex Systems, Proceedings of the International Conference on Systems, IEEE, pp. 847-852.

Quing Zhu, et al., "Combined Ulrasound and Near Infrared Diffused Light Imaging," Oct. 5, 1997, Ultrasonics Symposium, IEEE, pp. 1401-1405.

Sackmann E. E., et al., "Supported Membranes on Soft Polymer Cushions: Fabrication, Characterization and Applications," Trends in Biotechnology, vol. 18, No. 2, Feb. 2000, pp. 58-64.

International Search Report corresponding to International Application No. PCT/BE2004/000090 filed Jun. 21, 2004.

* cited by examiner

FIG. 6

APPARATUS AND METHODS FOR SIMULTANEOUS SURFACE ACOUSTIC WAVE AND SURFACE PLASMON RESONANCE MEASUREMENTS

CROSS-REFERENCE TO RELATED APPLICATIONS

This application is a continuation, under 35 U.S.C. § 120, of International Patent Application No. PCT/BE04/00090 filed Jun. 21, 2004 under the Patent Cooperation Treaty (PCT), which was published by the International Bureau in English on Dec. 29, 2004, with International Publication Number WO 2004/113882 A1, which designates the United States and claims the benefit of EP Application No. 03447165.6, filed Jun. 20, 2003. All above-referenced prior applications are incorporated by reference herein in their entirety and are hereby made a portion of this specification.

BACKGROUND OF THE INVENTION

1. Field of the Invention

The invention relates to the field of physical, chemical and bio-sensing. More specifically, the invention relates to methods and systems for determining physical properties related to density, refractive index, composition of mixture or layer thickness of bio-related materials.

2. Description of the Related Art

Optical methods for determination parameters related to the refractive index properties of materials are well known. The most common optical techniques for bio-sensing and determining refractive index related properties of bio-related materials are surface plasmon resonance (SPR) and ellipsometry. The qualities of surface plasmon resonance (SPR) as well accepted direct detection technique for monitoring biological processes are described in more detail by Liedberg et al., in Sensors and Actuators, 4 (1983) 299-304. Ellipsometry often is used for analysing thin film properties as described by Hook et al. in Anal. Chem. 73 (2001) 5796-5804. Nevertheless, monitoring biochemical reactions in a liquid medium is less evident due to the varying environment through which the probing light beam has to propagate. A typical configuration for performing surface plasmon resonance measurements for liquid-phase sensing is the Kretschmann configuration, well known by a person skilled in the art. In this configuration, the laser generating the SPR evanescent wave is only propagating through the substrate, leading to a better control over the influence of the various buffer solutions used during a protein adsorption experiment.

For monitoring bound mass changes in liquid media, the use of various acoustic wave devices is well known and e.g. described by Gizeli in Biomolecular Sensors, Ed. E. Gizeli and C. R. Lowe (Taylor & Francis, London), 2002. Love mode devices are particular types of shear wave—surface acoustic wave devices using an overlayer with low shear wave velocity that helps trap the acoustic energy near the surface, thus increasing the sensitivity. The devices based on the propagation of a guided shear acoustic wave, present sensitivity improvements over the more usual quartz crystal microbalance as well as a compatibility with measurements in liquids.

Combined optical and acoustic measurements for material characterisation are described by Laschitsch A. et al. in Appl. Phys. Letters 77 (2000) 2252-2254. The document describes the combination of surface plasmon resonance spectroscopy and quartz crystal microweighing to determine the optical thickness and the acoustic thickness. By studying the ratio of the optical and the acoustical thickness, information related to the layer density is obtained which can be used for structural investigations and screening applications. Unfortunately, the method described in this document only allows to obtain density related information and not to obtain real values for the physical properties such as density, refractive index, layer thickness and possibly mixture composition.

SUMMARY OF THE INVENTION

One embodiment includes a method and system for determining values of physical quantities for several characterising properties of a substance.

In a first aspect the invention relates to a method for analysing physical properties of a substance, the method comprising obtaining optical data related to the refractive index and the thickness of said substance, obtaining acoustical data related to the density and the thickness of said substance and entering the acoustical and optical data into a model of the optical/acoustical properties of the substance to thereby determine any of the thickness, the density, the refractive index and composite related information. The data related to the refractive index and the thickness of said substance typically may be data depending at the same time both on the refractive index and the thickness, i.e. the data may reveal a functional behaviour between the refractive index and the thickness. The data related to the density and the thickness of said substance typically may be data depending at the same time both on the density and the thickness, i.e. the data may reveal a functional behaviour between the density and the thickness.

The determined composite related information may comprise the rigid mass component and the viscous component.

The thickness of said substance may comprise information about the coverage of a substrate by said substance. The model may be an analytical model.

The substance may comprise one component. Alternatively, the substance may comprise two or more components. The substance may be a material in a solid or a liquid phase. The substance may be transparent or translucent. Alternatively, the substance may be not transparent and/or not translucent. The substance may be any of a mixture, a solution or an alloy. The substance may be a solution of organic or polymeric materials, e.g. biological material or biomolecules such as DNA, RNA, proteins, phosopolipids, lipids, cell lysates or fragments thereof.

Determining any of the thickness, the density, the refractive index and composite related information may comprise analysing the kinetics, found in either one of said optical data or said acoustical data, for instance by having slope determination routines. Determining any of the thickness, the density, the refractive index and composite related information may also comprise determining optima found in either one of said optical data and said acoustical data, and deriving information on the species within said substance from the position of said optima along a time axis. Determining any of the thickness, the density, the refractive index and composite related information may comprise using a look-up table for determining any of the thickness, the density, the refractive index and composite related information, whereby the look-up table may be based on previously obtained optical data and previously obtained acoustical data. Using the look-up table for determining any of the thickness, the density, the refractive index and composite related information may comprise interpolating said previously obtained optical data and/or said previously obtained acoustical data to match the obtained optical data and obtained acoustical data.

Obtaining optical data may comprise generating optical data of said substance on a surface. Generating optical data thereby may be performed by surface plasmon resonance measurements on the surface. Generating optical data alternatively or in addition thereto may be performed by any of a transmission measurement, a reflection measurement or an ellipsometry measurement.

Obtaining acoustical data may comprise generating acoustical data of the substance on a surface by generating acoustic waves guided towards the surface and sensing acoustic waves. The sensed acoustic waves thereby are influenced by the substance present at the surface. The acoustic waves may be guided towards the surface via a guiding layer which may e.g. be silicon oxide.

The invention furthermore also relates to an apparatus capable of analysing the interaction of a substance on a surface, the apparatus comprising a means for obtaining optical data related to the refractive index and the thickness of said substance, a means for obtaining acoustical data related to the density and the thickness of said substance and a calculation means for calculating any of the thickness, the density, the refractive index and composite related information of said substance based on a model of the optical/acoustical properties of the substance and on said obtained optical data and said obtained acoustical data. The composite related information of said substance may include the rigid mass component and the viscous component of said substance. The model used may be an analytical model.

The substance may comprise one component. Alternatively, the substance may comprise two or more components. The substance may be in a solid phase or in a liquid. The substance may be transparent or translucent. Alternatively, the substance may be not transparent and/or not translucent. The substance may be any of a mixture, a solution or an alloy. The substance may be a solution of organic or polymeric materials, e.g. biological material or biomolecules such as DNA, RNA, proteins, phosopolipids, lipids, cell lysates or fragments thereof.

The calculation means may be adapted for analysing the kinetics, found in either one of said optical data or said acoustical data, for instance by having slope determination routines. The calculation means may be adapted for determining optima found in either one of said optical data or said acoustical data, and deriving information on the species within said substance from the position of said optima along a time axis. The information on the species may be information about the amount of the species. The calculation means may comprise a look-up table for determining any of the thickness, the density, the refractive index and composite related information. The look-up table may be based on previously obtained optical data and previously obtained acoustical data. The calculation means may furthermore be adjusted for interpolating said previously obtained optical data and/or said previously obtained acoustical data to match the obtained optical data and obtained acoustical data.

The means for obtaining said optical data may comprise a means for generating the optical data. The means for obtaining said acoustical data may comprise a means for generating acoustical data.

The apparatus may comprise the surface, the surface having a sensing layer for sensing said substance. The sensing layer may comprise a recognition layer influencable by interaction with said substance. The thickness of the substance may comprise information about the coverage degree of the surface by said substance.

The means for generating said optical data may be any of a means for performing a transmission measurement, a reflection measurement or an ellipsometry measurement. The means for generating said optical data may comprise a means for performing surface plasmon resonance measurements. The means for performing surface plasmon resonance measurements may comprise an electromagnetic wave propagating device. The electromagnetic wave propagating means may be made of glass of quartz material. The electromagnetic wave propagating device may be a prism. The means for generating said optical data may exploit a plurality of electromagnetic wave sources. The means for generating said optical data may exploit an electromagnetic wave source, having a plurality of wavelengths.

The means for generating said acoustical data may comprise a first part for generating acoustic waves, guided to the surface and a second part for acoustic wave sensing. The apparatus furthermore may comprise a means for performing an electrochemical calibration.

In the apparatus, at least one of a material or geometric characteristic of said means for generating optical data or of said means for generating acoustical data may be adjusted to substantially reduce interference between said optical data and said acoustical data. The material characteristics may e.g. be the refractive indices. The geometric characteristics may e.g. be the thickness and the relative positions.

The calculation means may comprise a microprocessor, a microcomputer or a dedicated calculation means such as an ASIC or a programmable logic device, sometimes referred to as PAL, PLA, FPGA, PLD, EPLD, EEPLD, LCA or FPGA.

It is an advantage of the present invention that the method and system according to the present invention allows compatibility of the obtained physical quantities with both optical characteristics and mass-related characteristics.

It is furthermore an advantage of the present invention that it allows determination of the content of a mixture, based on a few propositions or a few basic measurements.

It is also an advantage of the present invention that the density, the refractive index, the layer thickness and the content of a mixture can be determined based on optical and acoustical measurements in combination with the use of a model.

It is furthermore an advantage of the present invention that the method and system allows identification of physical properties of bio-related mixtures, e.g. protein layer, and more specifically their water content.

Although there has been constant improvement, change and evolution of methods and systems in this field, the present concepts are believed to represent substantial new and novel improvements, including departures from prior practices, resulting in the provision of more efficient, stable and reliable methods and systems of this nature.

The teachings of the present invention permit the design of improved methods and systems for determining quantities of characterising properties of a substance, preferably a mixture.

These and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

In the different figures, the same reference signs refer to the same or analogous elements.

DETAILED DESCRIPTION OF THE PREFERRED EMBODIMENT

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

It is to be noticed that the term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In a first embodiment, a method is described for obtaining characterizing properties of a substance, based on modelling and combined acoustic and optical measurement data. The method comprises obtaining information from combined acoustic and optical measurements and using a model for determining the corresponding characterising properties. The method can be used to measure substances consisting of only a single component or substances comprising two or more components. Measurements can be performed on substances in liquid phase or in solid phase, on powders, etc. The substance may be a transparent or translucent material or a non-transparent or non-translucent material. The method is particularly oriented to characterisation of substances which are e.g. mixtures, alloys or solutions and is based on combined acoustical and optical measurement data. The substance may comprise organic or polymeric materials, e.g. biological material or biomolecules such as DNA, RNA, proteins, phosopolipids, lipids, cell lysates, or fragments thereof, etc. The measurement results obtained typically are obtained for a layer of substance being e.g. a mixture, an alloy or a solution although measurement results for other configurations could also be used, whereby e.g. a cavity filled with a substance is used.

In the present description, by way of example, illustration will be given for optical and acoustical measurement results obtained for a layer. These measurement results may be obtained e.g. for a deposited or adsorbed layer, although the invention is not limited thereto. Characterisation of substances such as e.g. mixtures, alloys or solutions can be done for every type of substance, where optical measurements can provide information related to the substance's refractive index and the thickness of the mixture layer and whereby acoustical measurements can provide information related to the substance's density and the thickness of the substance layer.

A typical example is characterisation of water content in protein layers, although the invention is not limited thereto. Estimation of water content in protein layers is an important topic in the development of biosensors, since the detection sensitivity is directly related to the number of active sites on the surface of the sensor to which receptor molecules are bound. When physical measurements of this bound layer are performed, such as via SPR or acoustic measurements, a large water content will lead to overestimates of the potential detection limit of the biosensor due to an overestimate of number of molecules bound to the surface. From a more fundamental point of view, determining water level content should provide more accurate physical parameters of the protein layer itself such as density and optical index by allowing the subtraction of the influence of water once it has been identified. The method is not only related to the determination of the content of a component in a substance such as e.g. a mixture, an alloy or a solution, it is also suitable for detection of the presence of a certain component in a mixture, alloy or solution, detection of the presence of a substance on a surface, obtaining values for the actual physical characteristics such as thickness, density or refractive index of a substance, measuring any physical change in thickness, density, refractive index, composition of a substance, etc. The method also can be used to study surface coverage by a substance.

Figure 1:
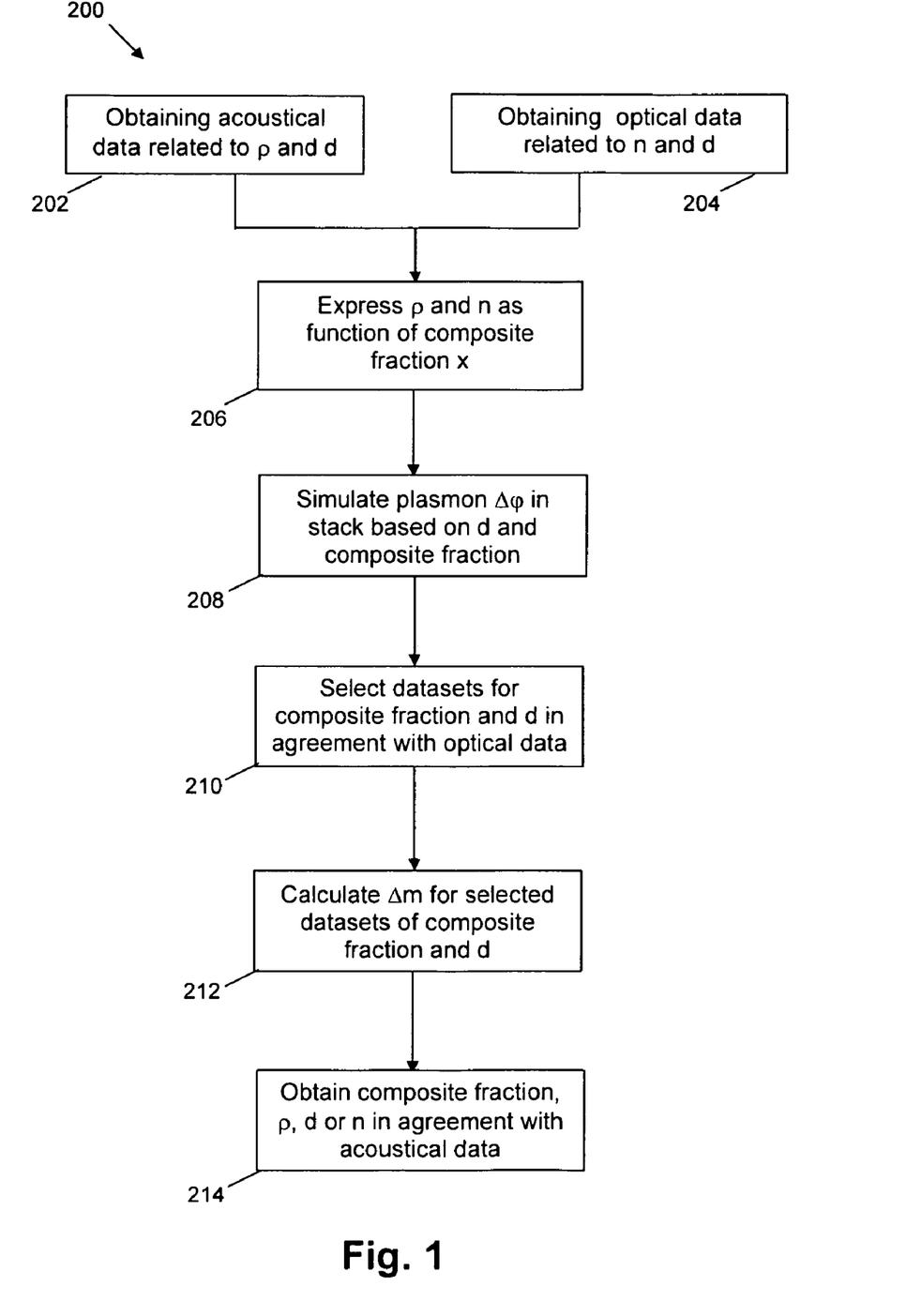
FIG. 1 shows a flow chart for a method for determining physical quantities of a mixture layer according to a first embodiment of the present invention.

An overview of the corresponding method is shown in FIG. 1. The method 200 comprises the steps of obtaining acoustical data 202 related to the density p and thickness d of the substance and of obtaining optical data 204 related to the refractive index n and the thickness d of the substance. Obtaining acoustical and optical data 202, 204 may be done in any suitable way, such as e.g. loading the results from a memory device, reading in the results from a measurement device, manually inserting the results e.g. by means of a keyboard or a keypad. Measurement results may originate from measurements on a static layer or time dependent measurements on a dynamically changing layer, e.g. during electrochemical or biochemical reactions or during treatment of the layer. In the latter case, it is important that both optical and acoustical measurements are related to the same material, such that preferably, the measurements are performed simultaneously. Different types of acoustical measurements can be used, such as e.g. quartz crystal microweighing and surface acoustic wave (SAW) measurements, but preferably a Love mode SAW technique is used for the present invention as this results in a better sensitivity. Different types of optical measurement techniques can also be used, such as e.g. ellipsometry, transmission/reflection measurements and surface plasmon resoncance (SPR) measurements. Preferably SPR measurements are used as these can be used for both transparent/translucent and non-transparent/non-translucent substances and as SPR measurements suffer less from influence of the environment if those measurement are performed in liquids. When SAW measurements are used, advantage is taken of the geometrical set-up of the surface acoustic wave (SAW) device, typically having a transparent backside free of electrodes. The latter allows easier accessibility for performing optical measurements in the sensing area. The set-up allows, during electrochemical and biochemical reactions or other physical change of the substance occurring on the sensing surface, simultaneous estimates of the bound mass changes based on the acoustical measurement and dielectric surface properties changes based on the optical measurements.

Figure 2:
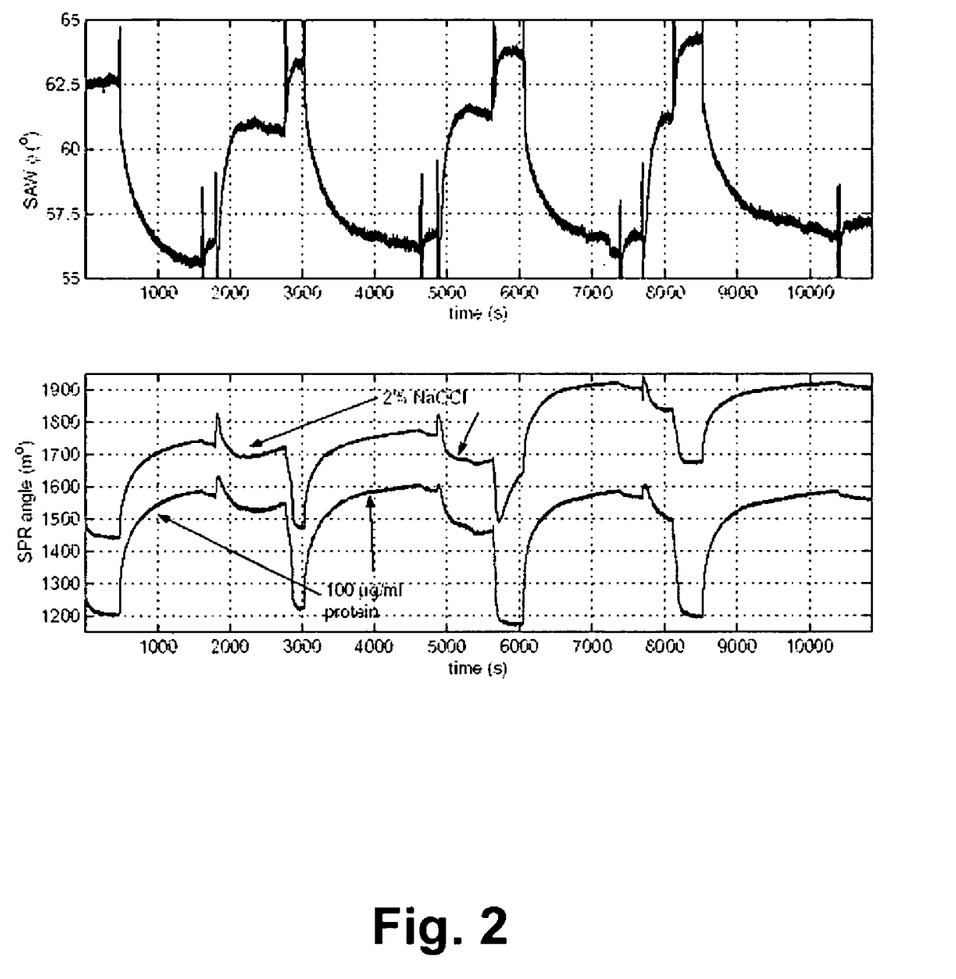
FIG. 2 shows the results of a combined simultaneous surface acoustic wave measurement and a surface plasmon resonance measurement according to the first and a second embodiment of the present invention.

By way of example, a non-limiting illustration is given for SAW acoustical measurements and SPR optical measurements of a mono-layer of proteins, the proteins having a density of 100 μg/ml adsorbed and desorbed—by providing 2% NaOCl—on a sensing surface of a system combining both measurements. Such a system is described in more detail in embodiment 3. A property of the protein used in the present example is that it only forms a mono-layer and will not stack to multiple layers even at high concentrations. The results for several adsorption and desorption steps is shown in FIG. 2. In the top graph, the measurement of the SAW phase at 123.200 MHz is shown while in the bottom graph the SPR angle shift is shown, both signals measured simultaneously. Repetitive steps of injection of a buffer solution, injection of the typical protein layers (100 □g/ml), injection of a buffer solution and removal of the protein mono-layer by injecting 2% NaOCl are shown.

After the steps of obtaining the optical and acoustical data 202, 204, the method 200 proceeds by using a model for determining values for the different characterising properties of the substance. The parameters required for analysing the acoustical, e.g. SAW, data are the layer thickness d and the layer density $\rho_{layer}$. The parameters required for analyzing the optical, e.g. SPR, data are the layer thickness d and the optical refractive index n of the substance studied. In this way, there are three unknown parameters being the density, the thickness and the refractive index of the substance and only two measurement results, i.e. the adsorbed mass per unit area and an SPR resonance angle shift which is a function of both n and d. To reduce the number of variables the method uses the following model. In step 206, the density and the refractive index are expressed as functions of the composite fraction based on assumptions made about the composite fraction dependency of the refractive index and the density of the mixture. The assumptions about the composite fraction dependency may be either a mathematical relationship or may be based on previously made optical and acoustical data of known mixtures. In the latter case a look-up table can be used, and interpolation of the results can be used to obtain the composite dependency for each density or each refractive index value. An example of a mathematical relationship is given by the assumption that the mixture is a homogeneous mixture of two composite materials. The mixture density $\rho_{mixture}$ is then $$\rho_{mixture} = x\rho_{composite\,mat1} + (1-x)\rho_{composite\,mat2}$$

Returning to the example of determining the water content in a protein layer the first composite material present with a fraction x can e.g. be the protein, and the second composite material present with a fraction (1−x) can be water. In this case $\rho_{protein}$ is assumed to be in the 1.2 g/cm$^3$ to 1.4 g/cm$^3$ range, based on literature values, and $\rho_{water}$=1 g/cm$^3$ is the density of water. In similar way the refractive index n mixture can be expressed as a function of the refractive indices of the two composite materials, i.e., $$n_{mixture} = xn_{composite\,mat1} + (1-x)n_{composite\,mat2}$$

For the example of determining the water content in a protein layer, the optical refractive index of the protein is assumed to be in the range $n_{protein}$=0.45 to 1.465 range, based on literature values, and the refractive index of water is $n_{water}$=1.33. In this way the parameters density, refractive index, layer thickness and composite fraction are reduced to the layer thickness and composite content x or water content proportion 1−x. The illustration of a homogeneous mixture of two composite materials is shown only by way of example and it will be obvious for a person skilled in the art that other mathematical relationships can be provided.

In step 208 of method 200, a simulation is made of the SPR angle shift in the measurement device and the mixture substance present at the sensing surface of the measurement device. This simulation allows prediction of the SPR angle shift as a function of the composite fraction x and the layer thickness d. These simulations may be performed following the formalism in which each component of the electrical field is propagated through a stack with planar dielectric interfaces. The simulation typically is based on an analytical model. As in principle only propagation will occur in transparent layers, it is sufficient to limit the stack to those layers of the device and the present mixture substance which can be reached by the incident optical beam without crossing a metal layer. The mixture substance thereby forms an additional dielectric layer. Optionally, the simulation of the surface plasmon resonance phase shift may be based on the full stack of planar layers, including metal layers, to include possible interference effects.

Figure 3:
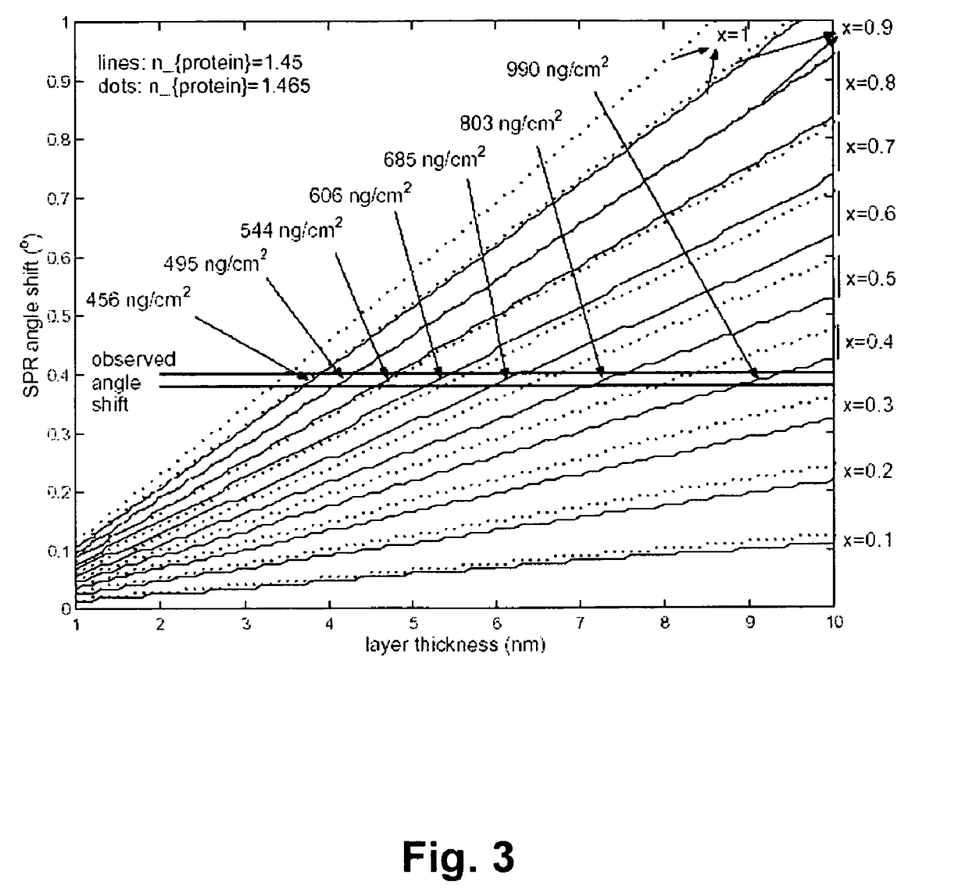
FIG. 3 shows a simulation of the surface plasmon resonance angle shift for varying protein layer thickness as can be obtained with the systems and methods as described in embodiments of the present invention.

By way of example, the simulation is illustrated for the determination of the water content in a protein layer. A stack of planar multilayers comprising a number of layers present in the measurement device and the mixture layer to be studied is simulated. FIG. 3 shows the simulation results for a glass substrate having nglass=1.518, a 1200 nm silicon dioxide layer having nSiO2=1.45, a 2 nm titanium layer having nTi=2.76+i3.84, a 50 nm gold layer having nAu=0.14+i3.697 and the mixture layer of proteins and water. It will be obvious to the person skilled in the art that the layers used in the simulation will depend on the specific measurement set-up used. The angle shift as a function of water content and layer thickness is illustrated for two slightly varying refractive indices for the proteins. The simulation results are shown as a function of the composite fraction x and the layer thickness.

In step 210, the obtained simulation results are compared with the optical data obtained in step 204. The SPR data obtained in step 204 are indicated in FIG. 3, and comparison allows to obtain a set of pairs of values for the composite fraction x and the layer thickness d which are compatible with the obtained optical data, obtained during step 204.

Figure 4:
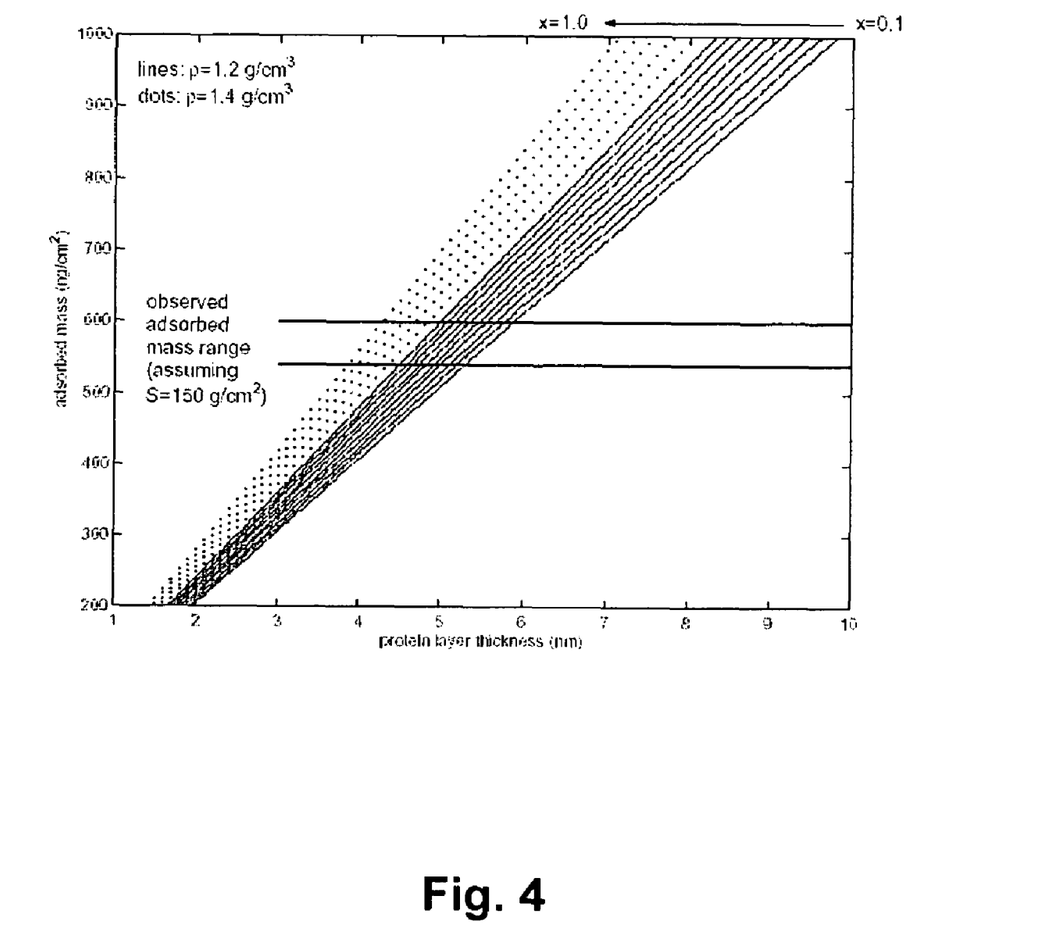
FIG. 4 shows a simulation of the surface acoustic wave frequency shift for varying protein layer thickness as can be obtained with the systems and methods as described in embodiments of the present invention.

In step 212, the obtained set of pairs of values for the composite fraction x and the layer thickness d is used for calculating the mass per unit area, i.e. Δm=ρd. For the example of determining the water content in a protein layer, the results of these calculations are shown in FIG. 4. In this figure, the results are shown for slightly differing refractive indices for the proteins, based on values found in the literature, i.e. from 1.45 (indicated with solid lines) to 1.465 (indicated with dots). The simulation results are shown for varying protein layer thickness (indicated at the abscissa) and for varying proportion of proteins in the layer (from x=10% to x=100% from bottom to top). The mass density of the points lying in the region of the obtained optical data are indicated for added clarity.

In step 214, the obtained calculated values for the mass per unit area are compared with adsorbed mass based on the acoustical data obtained in step 202. This allows to determine a unique set of parameters for the composite fraction, the thickness and thus also the refractive index and the density, which are compatible with both the optical data and the acoustical data.

For the example of determining the water content in a protein layer, this can be seen in FIG. 4. In this figure, the results are shown for two slightly differing densities for the proteins, based on values found in the literature, i.e. from 1.2 g/cm$^3$ (indicated with solid lines) to 1.4 g/cm$^3$ (indicated with dots). The results are shown for varying protein layer thickness (indicated at the abscissa) and varying proportion of proteins in the layer (from x=10% to x=100% from right to left). In the case under consideration here, an observed angle shift of 0.380 to 0.400° and an adsorbed mass of 540 to 580 nanogram/cm$^2$ is only compatible with x=0.75±0.15 and d=4.7±0.7 nm. The thickness result is compatible with atomic force microscope (AFM) measurements in liquid while the mass per unit area is compatible with morphological data obtained by electronic microscopy (not shown), performed as cross-check measurements.

While the main source of uncertainty is due to the wide possible values of the density and optical index reported in the literature, the experimental results display good reproducibility. The above mentioned method thus describes combination of measurement results based on adsorbed mass change measurements and based on surface dielectric properties variations, to identify physical properties of a substance, more specifically of a mixture. The method is especially suitable for the identification of physical properties of protein layers, such as e.g. their water content. Amongst these physical properties are both the bound mass as well as the dielectric changes occurring during protein adsorption. It is an advantage of the present invention that the method is especially suitable for monitoring biological processes.

In a further embodiment, a method is described comprising the same features and steps as the measurement method described in the first embodiment, whereby the measurement results are generated by the system and an additional step of calibrating the mass sensitivity of the measurement means is performed. The calibration step typically is performed prior to the actual measurement phase. Such a calibration especially is needed if the measurement is to be operated in a liquid medium. The calibration is performed by supplying a known amount of mass to the sensing surface and studying the corresponding SAW signal. A possible way to provide a known amount of mass can e.g. be electro-depositing a metal, such as e.g. copper, on the sensing surface. It will be obvious for the person skilled in the art that any way of providing a known amount of mass to the sensing surface can be used and that the method is not limited to electro-depositing.

By way of example the calibration procedure will be illustrated for the electro-deposition of copper on the sensing surface. The electro-deposition of copper may e.g. be performed by providing a pseudo-reference electrode being a copper wire, providing a counter electrode which may e.g. be a platinum wire and providing a solution of 10$^{-2}$ M CuSO$_4$ in 10$^{-2}$ M H$_2$SO$_4$. The deposition typically is controlled using a potentiostat, like e.g. the PC3-300 potentiostat as available from Gamry Instruments (Warminster, USA). It will be obvious for a person skilled in the art that the exact parameters with which the electro-deposition is performed are not limiting the present invention.

Figure 5:
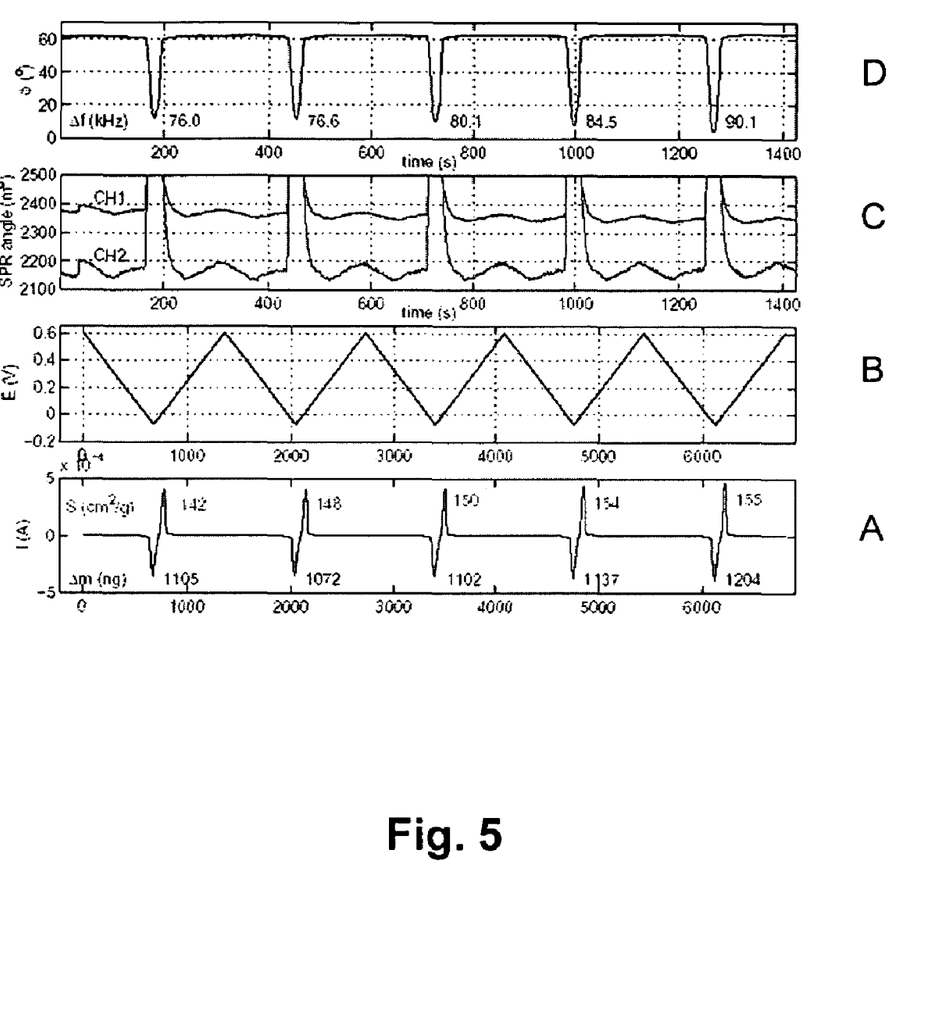
FIG. 5 shows a set sensitivity calibration curves using copper electro-deposition for surface acoustic wave measurements, as used in the first and second embodiments of the present invention.

An overview of the different measured signals is shown in FIG. 5. In graph A and graph B, the potentiostat current and the potential versus a copper wire acting as a pseudo reference electrode with the Cu$^{2+}$ ions in solution is shown. The equivalent mass, corresponding with the potentiostat current, and the corresponding calculated sensitivity is indicated in graph A. In graph C, the surface plasmon resonance angle shift is shown. In the example, measurement is performed using two different measurement channels, an optional second measurement channel being used to confirm the measurement result of the first measurement channel. In graph D, the surface acoustic wave phase, monitored at a fixed frequency, i.e. 123.200 MHz, is converted into a frequency using the linear phase-to-frequency relationship. The frequency shifts, expressed in kHz, corresponding with the SAW phase shifts are indicated in graph D for each large SAW phase shift. During the electro-deposition of copper, the surface plasmon resonance (SPR) displayed resonance angle shifts due to the varying potential. When the voltage applied by the potentiostat is above 0.2 V with respect to the Cu pseudo reference electrode, the SPR angle slightly shifts due to the electro-reflectance effect, known by the person skilled in the art. Below 0.2V, under potential deposition starts depositing a mono layer of Cu atoms on the Au surface. A phase shift of the SAW device occurs and a reversal of the trend of the angle shift of the SPR can be seen (FIG. 5, graph C). Below 0 V, a rough Cu layer is deposited, leading to a loss of the SPR peak and a large phase shift of the SAW device due to the large added mass, as can be seen in FIG. 5 graphs C and D. The rough, discontinuous film of copper clusters a few tens to hundreds of nanometers high. This was also observed by in-situ atomic force microscopy imaging, not shown in the drawings. The large phase shift of the SAW device is displayed as a frequency drop Δf, caused by the added mass Δm, added to the sensing surface. The electro-deposited mass can be determined based on a current measurement from the potentiostat over a period δt, leading to a direct estimate of the electro-deposited mass Δm:

$$\Delta m = \frac{\Sigma_j I_j \times \delta t}{F} \times \frac{M}{n_e}$$

where F=96485C is the Faraday constant, M the molar weight of the electro-deposited metal and n$_e$ the number of electrons exchanged for each metallic atom reduced. The mass sensitivity S of the system can be determined from the amount of added mass Δm and the frequency difference Δf:

$$S = \frac{\Delta f}{f_o} \frac{A}{\Delta m}$$

where A=0.49×0.54 cm$^2$ is the area of the sensing working electrode and f$_0$=123.200 MHz the base frequency of the SAW device. The resulting sensitivity for the Love mode device under consideration here is 150±15 cm$^2$/g. It will be obvious for the person skilled in the art that the calibration based on Cu electro-deposition is given by way of example and that the use of other materials or other techniques can be used as well. It is an advantage of the present embodiment that it allows performing a calibration of the system such that the sensitivity of the system can be determined.

Figure 5A:
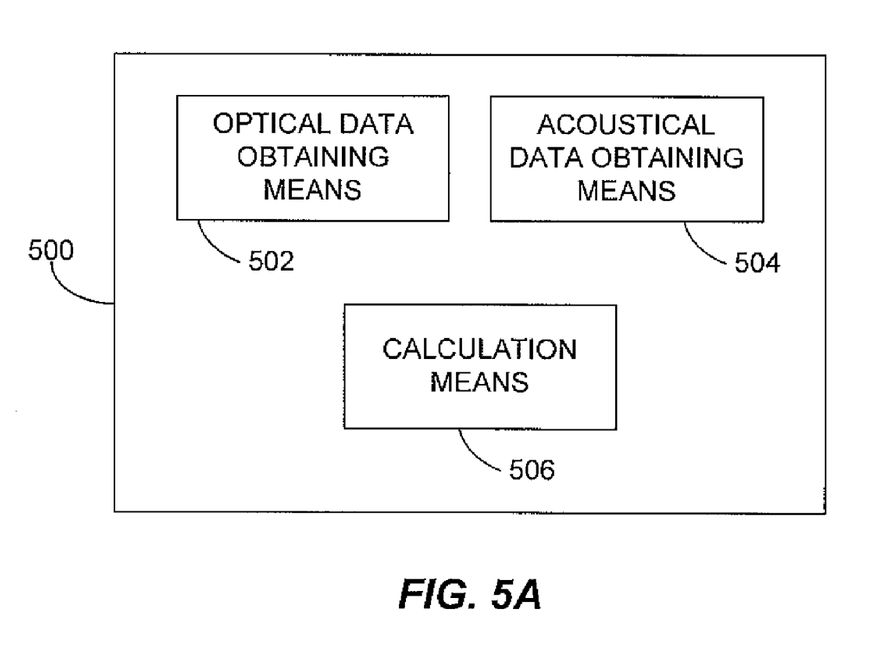
FIG. 5A shows a block diagram of a system which may perform the method described in F*igure* 1.

Referring now to FIG. 5A. in a further embodiment the invention relates to a system 500 for performing the methods as described in the previous embodiments for obtaining characterizing properties of a substance, based on combined acoustic and optical measurement data and modelling. The system typically comprises a means for obtaining optical data 502, a means for obtaining acoustical data 504 and a calculation means 506 for determining any of the refractive index n, the composite fraction x, the density ρ or the thickness d of the studied substance, which preferably is a mixture layer, based on a model of the optical and acoustical properties of the substance and on said obtained optical data and said obtained acoustical data. The calculation means may be any processing means having sufficient power to perform the modelling. This may e.g. be a microprocessor, a microcontroller, a DSP, a GPP, an ASIC or a programmable logic device such as e.g. a PAL, a PLA, an FPGA, a PLD, an EPLD, an EEPLD, an LCA or an FPGA. These means are adapted for expressing the density ρ and the refractive index a as a function of the composite fraction x. This includes e.g. adaptation such that an analytical mathematical relationship for the dependency of the refractive index n and the density ρ of the composite fraction x can be applied or e.g. adaptation such that a look-up table can be used for expressing the refractive index n and the density ρ as a function of the composite fraction x. Such a look-up table may be based on previously measured acoustical and optical data for a set of standard known mixtures, and the processing means may be further adapted to allow interpolation for densities or refractive indices where no information is present in the look-up table. Besides adaptation for expressing the density p and refractive index a as a function of the composite fraction x, the calculation means furthermore may be adapted for performing simulation of the surface plasmon resonance phase shift for a given measurement device and a measured substance. These simulations may be performed following the formalism in which each component of the electrical field is propagated through a stack with planar dielectric interfaces, the stack comprising the relevant layers of the measurement device and the measured substance. Typically, these simulations require the input of refractive indices and thicknesses of the layers representing the measurement device. As in principle only propagation will occur in transparent layers as the optical beam will otherwise be absorbed or reflected, it is sufficient to limit the stack to those layers which can be reached by the incident optical beam without crossing a metal layer. Therefore limiting the simulation to the dielectric layers often is sufficient.

Optionally, the simulation of the surface plasmon resonance phase shift may be based on the full stack of planar layers to include possible interference effects. The simulation is performed as a function of the composite fraction x and the layer thickness d. The calculation means furthermore may be adapted for selecting the data sets of the composite fraction x and the layer thickness d which are in agreement with the obtained optical data. The calculation means furthermore may be adapted for determining, i.e. calculating, the surface density of the layer for the selected data sets of the composite fraction x and the layer thickness d and for comparing the generated surface density data with the obtained acoustical data. It is to be noted that the adaptation of the means may be such that the calculation may be performed automatically. On the other hand the adaptation of the calculation means may also be such that the calculation is performed based on a minor interaction by the user or that it is rather a guiding means wherein the user initiates the different steps of the calculation.

The means for obtaining optical data and the means for obtaining acoustical data may be either only input means for loading the data of optical and acoustical measurements or these may include means for performing optical measurements and/or acoustical measurements. The means for loading typically are input ports allowing to receive information from e.g. a memory device, a storage device or an external measurement device.

The means for performing optical measurements may be any optical measurement device allowing to obtain information related to thickness d of the measured substance and the refractive index n, e.g. an ellipsometry set-up, a transmission/reflection measurement set-up, a surface plasmon resonance (SPR) set-up. Using a surface plasmon resonance set-up is favourable, as SPR measurements can be used for both transparent and/or translucent and non-transparent and/or non-translucent materials and as these suffer less from influence of the environment if measurement in liquids are performed.

The means for performing acoustical measurements may be e.g. a quartz crystal microweighing system or a surface acoustic wave (SAW) system. Preferably a Love mode SAW system is used as this allows a better sensitivity. When SAW measurements are used, advantage is taken of the geometrical set-up of the surface acoustic wave (SAW) device, typically having a transparent backside free of electrodes. The latter allows easier accessibility for performing optical measurements in the sensing area. If optical and acoustical data are to be obtained for a dynamic changing substance, it is advantageous to measure both optical and acoustical data simultaneously on the same substance.

Figure 6:
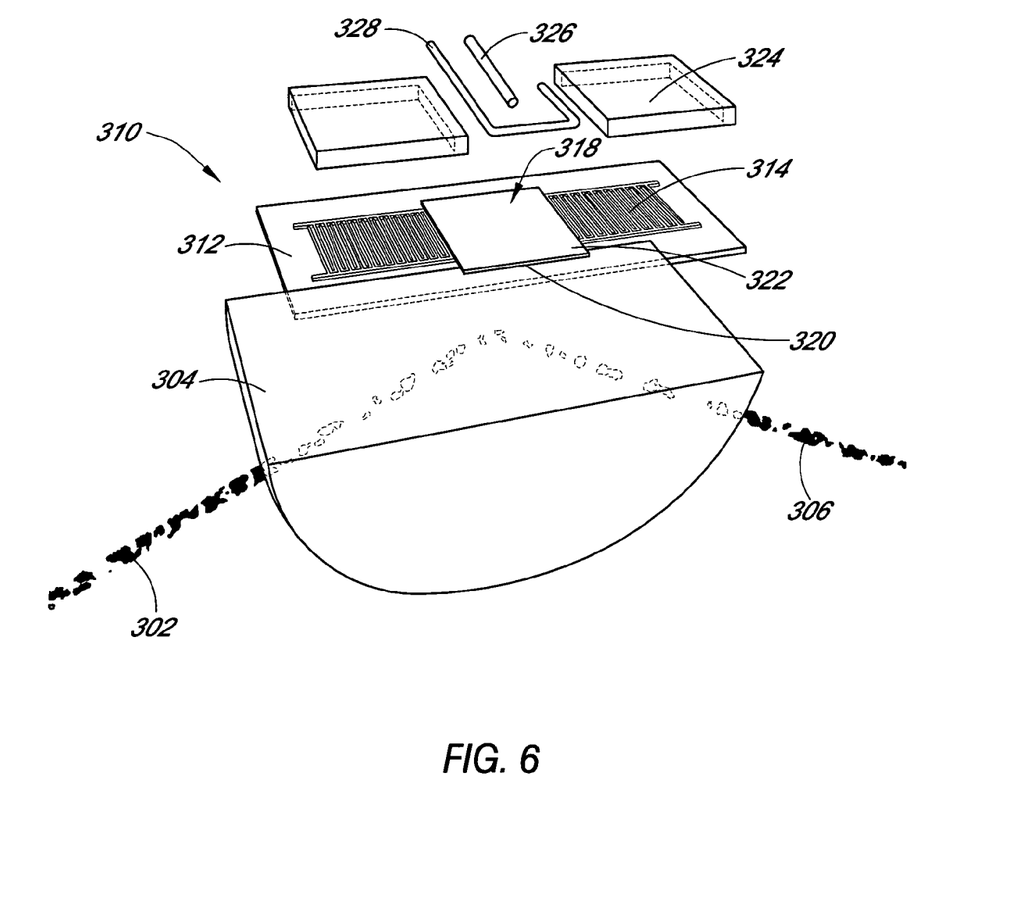
FIG. 6 shows an elevated top view of an experimental set-up for performing a simultaneous optical measurement and acoustic measurement according to a third embodiment of the present invention.

By way of example, an illustration is given of a system that can be used as means for generating optical and acoustical data. The system comprises a modified commercial SPR instrument (IBIS II, IBIS Technologies BV, The Netherlands) to detect the surface plasmon resonance angle after replacing its gold coated glass slide by a Love mode SAW device. Nevertheless, the means for generating optical and acoustical data is not limited thereto and other systems based on other techniques optical and acoustical techniques can be used as well, as will be obvious to a person skilled in the art. Part of the system is illustrated in FIG. 6. The system comprises a light source (not shown), which typically is a laser. In the IBIS II system, the excitation laser has a laser beam with a wavelength of 670 nm. The excitation laser beam 302 is injected through a means for guiding 304 the excitation laser beam to the sensing surface. The means for guiding 304 preferably is a prism made of glass or quartz. The reflected laser beam 306 is detected using a detection system (not shown) as a function of the angle. In the present instrument, this is done by scanning a 6° angle span recorded with a 200 pixels CCD array. The obtained curves are fitted by a polynomial to extract with high accuracy the position of the dip. The system furthermore comprises an acoustic wave device 310 made of a 500 μm thick single terminated-cut quartz wafer or quartz substrate 312 on which interdigital transducers 314 are patterned, thus allowing generation of acoustic waves. The interdigital transducers 314 may e.g. be 200 nm thick sputtered Al interdigitated electrodes. The surface of the quartz wafer with interdigital transducers is coated by a guiding layer (not shown), e.g. a silicon dioxide layer, for guiding the surface acoustic waves to the substance to be measured. This may e.g. be a 1.13 μm PECVD silicon dioxide layer (not shown). The sensing area 318, which may have any suitable area, like e.g. 4.9×5.4 mm², may be coated with a suitable coating layer, such as a Ti layer 320 with a thickness in the range of 0 nm to 15 nm and an Au layer 322 with a thickness in the order of 50 nm Au. This sensing area 318 acts both as a working electrode for electrochemistry or a grounded electrode during biochemical experiments, as well as a supporting layer for the surface plasmon resonance generation. The contact between liquid and transducers is prevented by a contact prevention means 324 which may e.g. be glass slides supported by walls such as e.g. SU8 epoxy walls. The phase of the SAW delay line is monitored at a fixed frequency using any suitable monitoring device, such as a network analyzer, e.g. HP4396A at 123.200 MHz. The phase shift is converted to a frequency shift thanks to the linear phase to frequency relationship recorded in the Bode plot. The observed phase shift leads to a frequency shift (as would be observed in a phase locked loop configuration) which in turn can be converted to an adsorbed mass change through the sensitivity of the device. For calibration reasons, a reference electrode 326, e.g. of Cu, and a counter electrode 328, e.g. of Pt, may be provided, depending on the method of calibration used.

The influence of the SAW device substrate over the detection of the SPR is limited to interference patterns due to the birefringence of the quartz substrate 312, and the optical index mismatch between the quartz substrate 312 and the deposited guiding layer, e.g. silicon dioxide layer. The former effect is reduced by orienting the optical axis of the quartz substrate 312 so that it is in the plane defined by the normal to the sensing surface and the wavevector of the laser, thus minimizing the optical index difference between the ordinary and the extraordinary axis. The remaining interference patterns lead to fringes with a low enough contrast so that the surface plasmon peak is easily identified and tracked during the experiments. The apparatus is so designed as to substantially reduce interference between said acoustical, e.g. surface acoustic wave, measurements and said optical, e.g. surface plasmon resonance, measurements, in particular the interference patterns are reduced by optical orientation of the crystal (quartz) 312 used. It is an advantage of the present invention that it does not only provide a method and apparatus for studying the composition of a mixture but that it also provides a method and an apparatus for detecting the presence of a substance on a surface. It is furthermore an advantage of the above described system that it allows combining two independent measurement methods which can be performed at the same time, substantially without much interference between the two methods.

It is an advantage of the present invention that the combination of optical and acoustical data, together with the use of a model allows determination of the water content and layer thickness in protein layers.

Other arrangements for accomplishing the objectives of the methods and systems for determining characterising properties based on optical and acoustical data embodying the invention will be obvious for those skilled in the art. It is to be understood that although preferred embodiments, specific constructions and configurations, as well as materials, have been discussed herein for the methods, systems and devices according to the present invention, various changes or modifications in form and detail may be made without departing from the scope and spirit of this invention. For example, although the calculation has been described as simulating the SPR phase shift, comparing the results with the obtained optical data and using selected results for comparison with the acoustical data, alternatively calculation can also be performed by simulating the acoustical measurement i.e. simulating the change in bound mass and comparing the results with the obtained acoustical data followed by using the selected results for comparing with the optical data.

What is claimed is:

1. A method of analysing physical properties of a substance, the method comprising:

obtaining optical data related to the refractive index and the physical thickness of said substance;

obtaining acoustical data related to the density and the physical thickness of said substance; and entering the acoustical and optical data into a model of the optical/acoustical properties of the substance to thereby determine any of the physical thickness, the density, the refractive index or composite fractions of the substance.

2. The method of claim 1, wherein said composite fractions of the substance comprises a rigid mass component fraction and a viscous component fraction.

3. The method of claim 1, wherein said determining comprises analysing the kinetics, found in either one of said optical data or said acoustical data.

4. The method of claim 1, wherein said determining comprises determining optima found in either one of said optical data and said acoustical data and deriving information on the species within said substance from the position of said optima along a time axis.

5. The method of claim 1, wherein said determining comprises using a look-up table for determining any of the physical thickness, the density, the refractive index or composite fractions of the substance, said look-up table based on previously obtained optical data and previously obtained acoustical data.

6. The method of claim 5, wherein using a look-up table for determining any of the physical thickness, the density, the refractive index or composite fractions of the substance comprises interpolating said previously obtained optical data and/or said previously obtained acoustical data to match the obtained optical data and obtained acoustical data.

7. The method of claim 1, wherein said obtaining optical data comprises generating optical data of said substance on a surface.

8. The method of claim 7, wherein said generating optical data comprises performing surface plasmon resonance measurements on said surface.

9. The method of claim 1, wherein said obtaining acoustical data comprising generating acoustical data of said substance on a surface by generating acoustic waves guided towards said surface and sensing acoustic waves from said substance.

10. An apparatus configured to analyse the interaction of a substance on a surface, the apparatus comprising:

means for obtaining optical data related to the refractive index and the physical thickness of said substance;

means for obtaining acoustical data related to the density and the physical thickness of said substance; and calculation means for calculating any of the physical thickness, the density, the refractive index or composite fractions of said substance based on a model of the optical/acoustical properties of the substance and on said obtained optical data and said obtained acoustical data.

11. The apparatus of claim 10, wherein said composite fractions of said substance includes a rigid mass component fraction and a viscous component fraction.

12. The apparatus of claim 10, wherein said calculation means is adapted for analysing the kinetics, found in either one of said optical data or said acoustical data.

13. The apparatus of claim 10, wherein said calculation means is adapted for determining optima found in either one of said optical data or said acoustical data and deriving information on the species within said substance from the position of said optima along a time axis.

14. The apparatus of claim 10, wherein said calculation means comprises a look-up table for determining any of the physical thickness, the density, the refractive index or composite fractions, said look-up table based on previously obtained optical data and previously obtained acoustical data.

15. The apparatus of claim 14, wherein said calculation means furthermore is adapted for interpolating said previously obtained optical data and/or said previously obtained acoustical data to match the obtained optical data and obtained acoustical data.

16. The apparatus of claim 10, wherein the means for obtaining said optical data comprises a means for generating said optical data, and the means for obtaining said acoustical data comprises a means for generating said acoustical data.

17. The apparatus of claim 10, wherein said apparatus comprises the surface, the surface having a sensing layer for sensing said substance.

18. The apparatus of claim 17, wherein said sensing layer comprises a recognition layer influencable by interaction with said substance.

19. The apparatus of claim 16, wherein said means for generating said optical data is a means for performing surface plasmon resonance measurements.

20. The apparatus of claim 19, wherein said, means for performing surface plasmon resonance measurements comprises an electromagnetic wave propagating device.

21. The apparatus of claim 19, wherein said electromagnetic wave propagating device is a prism.

22. The apparatus of claim 16, wherein said means for generating said optical data exploits a plurality of electromagnetic wave sources.

23. The apparatus of claim 16, wherein said means for generating said optical data exploits an electromagnetic wave source, having a plurality of wavelengths.

24. The apparatus of claim 17, wherein said means for generating said acoustical data comprises a first part for generating acoustic waves, guided to said surface and a second part for acoustic wave sensing.

25. The apparatus of claim 10, furthermore comprising a means for performing an electrochemical calibration.

26. The apparatus of claim 16, wherein at least one of a material or geometric characteristic of said means for generating optical data or of said means for generating acoustical data is adjusted to substantially reduce interference between said optical data and said acoustical data.

27. The apparatus of claim 10, wherein the calculation means comprises a microprocessor.

28. An apparatus configured to analyse physical properties of a substance comprising:
    an electromagnetic wave propagating device configured to obtain optical data related to a refractive index and a physical thickness of the substance;
    a surface acoustic wave (SAW) system configured to obtain acoustical data related to the density and the physical thickness of said substance; and
    a processor configured to calculate any of the physical thickness, the density, the refractive index or composite fractions of said substance based on the obtained optical data and the obtained acoustical data.

* * * * *

UNITED STATES PATENT AND TRADEMARK OFFICE
CERTIFICATE OF CORRECTION

PATENT NO. : 7,440,085 B2  Page 1 of 1
APPLICATION NO. : 11/313606
DATED : October 21, 2008
INVENTOR(S) : Friedt et al.

It is certified that error appears in the above-identified patent and that said Letters Patent is hereby corrected as shown below:

Title page, Item (56), Page 2, Col. 2, Line 1, please change "Ulrasound" to --Ultrasound--.

Column 11, Line 11, please change "index a" to --index n--.

Column 11, Line 23, please change "p" to --$\rho$--.

Column 11, Line 24, please change "index a" to --index n--.

Signed and Sealed this

Ninth Day of June, 2009

JOHN DOLL
*Acting Director of the United States Patent and Trademark Office*